(12) United States Patent
Cho et al.

(10) Patent No.: US 8,431,364 B2
(45) Date of Patent: Apr. 30, 2013

(54) BIOPOLYMER PRODUCED BY FERMENTING THE EXTRACT OF SOYBEAN WITH FOLIC ACID AND A COMPOSITION CONTAINING THEREOF

(75) Inventors: Boo Sun Cho, Seoul (KR); Kwang Nyeon Kim, Yojngin-si (KR)

(73) Assignee: Damy Chemical Co. Ltd., Seoul (KR)

( * ) Notice: Subject to any disclaimer, the term of this patent is extended or adjusted under 35 U.S.C. 154(b) by 200 days.

(21) Appl. No.: 12/681,725

(22) PCT Filed: Oct. 2, 2008

(86) PCT No.: PCT/KR2008/005816
§ 371 (c)(1),
(2), (4) Date: Jul. 6, 2010

(87) PCT Pub. No.: WO2009/045064
PCT Pub. Date: Apr. 9, 2009

(65) Prior Publication Data
US 2011/0288025 A1    Nov. 24, 2011

(30) Foreign Application Priority Data
Oct. 5, 2007  (KR) .................. 10-2007-0100311

(51) Int. Cl.
*C12P 21/04* (2006.01)
(52) U.S. Cl.
USPC ........ 435/71.1; 435/71.2; 435/170; 514/17.2; 514/18.6; 424/93.46
(58) Field of Classification Search .............. 435/71.1, 435/71.2, 170; 514/17.2, 18.6; 424/93.4
See application file for complete search history.

(56) References Cited

U.S. PATENT DOCUMENTS

| 6,685,973 | B1* | 2/2004 | Kung-Ming | 424/757 |
| 2004/0043451 | A1* | 3/2004 | Yoneda et al. | 435/69.1 |
| 2010/0035881 | A1* | 2/2010 | Kaminuma et al. | 514/238.8 |

FOREIGN PATENT DOCUMENTS

| JP | 2003-026582 | 1/2003 |
| JP | 2003-327540 | 11/2003 |
| JP | 2006-001922 | 1/2006 |
| JP | 2006-193451 | 7/2006 |
| JP | 2006-316022 | 11/2006 |
| KR | 1020050094081 | 9/2005 |
| KR | 1020060124466 | 12/2006 |
| WO | 02/080862 | 10/2002 |

OTHER PUBLICATIONS

Rokshar et al. Dermatol. surg. (2005) 31:1166-1178.*
Machine translation for KR 723844 downloaded from the Korean Intelectual Property Office on Jul. 24, 2012.*
Shane, B. J. Biol. Chem. (1980) 255(12): 5649-5654.*
Harada, T. "Characteristics and applications of a polyfructan synthesized from sucrose by *Aspergillus sydowii* conidia"; (1993) *Food Hydrocolloids* 7(1):23-28 (Abstract only).
Hou, J-W et al."Changes in some components of soymilk during fermentation with bifidobacteria"; (2000) *Food Research International* 33:393-397.
Yao, R et al. "Effects of gamma-glutamyl hydrolase on folyl and antifolylpolyglutamates in cultured H35 hepatoma cells"; (1995) *molecular Pharmacology* 48(3):501-511. (Abstract only).
Japanese Office Action, dated Aug. 14, 2012, in Japanese Patent Application No. 2010-527888, a related application, 4 pp. (English translation included).
Agrahar-Murugkar et al. (2006) "Preparation Techniques and Nutritive Value of Fermented Foods from the Khasi Tribes of Meghalaya," Ecology of Food and Nutrition 45:27-38.
Japanese First Office Action, dated Jan. 15, 2013, in Japanese Patent Application No. 2010-527888, a related application, along with English translation, 4 pp.
Bailey, L.B. (1988) "Factors Affecting Folate Bioavailability," Food Technology 42:206-210, 212, 238.
Cichowicz et al. (1981) "Folylpoly-γ-Glutamate Synthesis by Bacteria and mammalian Cells," Molecular and Cellular Biochemistry 39:209-228.
Shin, et al. (1975) "Studies of Folic Acid Compounds in Nature. IV. Folic Acid Compounds in Soybeans and Cow Milk," Can. J. Biochem. 53(3):338-343.
Yao, et al. (1995) "Effects of γ-Glutamyl Hydrolase on Folyl and Antifolylpolyglutamates in Cultured H35 Hepatoma Cells," Molecular Pharmacology 48(3):505-511.

\* cited by examiner

*Primary Examiner* — Susan Hanley
(74) *Attorney, Agent, or Firm* — Lathrop & Gage LLP

(57) ABSTRACT

Provided are a folyl extract of fermented soybean (EFS) produced by fermenting a culture including a folic acid and soybean extract by using a microorganism, and a composition including the folyl EFS. The folyl EFS has an anti-histamine effect, an anti-allergic effect, a calcium-absorption-promotion effect, a bone-growth-promotion effect, a cell growth promotion effect, a collagen biosynthesis promotion effect, a wrinkle improvement effect, and an UV-induced cell damage inhibition effect. Accordingly, the folyl EFS can be used in a skin external application or cosmetic composition, a health supplement food composition, a feed composition, and a pharmaceutical composition.

6 Claims, 7 Drawing Sheets

BIOPOLYMER PRODUCED BY FERMENTING THE EXTRACT OF SOYBEAN WITH FOLIC ACID AND A COMPOSITION CONTAINING THEREOF

CROSS-REFERENCE TO RELATED APPLICATIONS

This application is the U.S. National Stage of International Application No. PCT/KR2008/005816, filed Oct. 2, 2008 and published in English on Apr. 9, 2009 as WO 2009/045064, which claims the benefit of Korean Patent Application No. 10-2007-0100311, filed Oct. 5, 2007, both of which are hereby incorporated by reference to the extent not inconsistent with the disclosure herewith.

TECHNICAL FIELD

The present invention relates to a folyl extract of fermented soybean (EFS) produced by fermenting a culture including a folic acid and soybean extract by using a microorganism, and a composition including the same.

The folyl EFS or composition according to the present invention has an anti-histamine effect, an anti-allergic effect, a calcium absorption acceleration effect, a bone growth acceleration effect, a cell growth acceleration effect, a collagen biosynthesis acceleration effect, a wrinkle-improvement effect, and an effect of inhibiting cell damage caused by ultra-violet (UV) radiation. Accordingly, the folyl EFS or composition according to the present invention can be used in skin external applications or cosmetic compositions, health supplement food compositions, feed compositions, or pharmaceutical compositions.

BACKGROUND ART

Chungkookjang and Natto are representative fermented foods and are produced by fermenting soybeans using *Bacillus subtilis*. When soybeans are fermented, γ-polyglutamate and polyfructan polymers are generated. γ-polyglutamate is known to have moisturizing and cell activation functions, and when used together with an anti-cancer drug such as Taxol, the effect of the drug used is increased. Polyfructan is a dietary fiber that is used to lose weight and when administered, gastric fullness and appetite suppression can occur and thus, obesity can be prevented. In addition, it is reported that polyfructan inhibits growth of harmful cells in bowels and helps *Bifidobacterium* grow (see Journal of Applied Microbiology, 92, 5, p 958-963).

Patents related to fermented soybeans include a patent related to a cosmetic material (see Korean Registration Patent No. 0451631), and a patent related to a skin external application (see Korean Publication Patent No. 2001-0083876). Seong mun-hoe et al. developed an enzyme-based technique for producing γ-polyglutamate having a molecular weight of 2,000 kDa or more (see App. & Environ. Microbiol. 2004; 70(7), 4249-4255; and Korean Registration Patent No. 10-0399091). Also, they registered a patent based on research results regarding a material in which an ascorbic acid binds to γ-polyglutamate having such a high molecular weight (Korean Registration Patent No. 10-0485727). However, a novel type of fermented soybean polymer in which a folic acid (also called as vitamin $B_9$) binds to γ-polyglutamate and an application thereof have not been developed.

Folic acid is known to be a material that lowers levels of homocysteine that is associated with heart disease and dementia of elderly people. Accordingly, when folic acid is used in foods for elderly people, high effects can be obtained. Folic acid naturally exists in a polyglutamate form and thus can be easily absorbed into bodies of animals and humans.

DESCRIPTION OF THE DRAWINGS

FIG. 1 is a series of microscopic images showing an anti-histamine effect of a folyl extract of fermented soybean (folyl EFS), wherein

DETAILED DESCRIPTION OF THE INVENTION

Technical Problem

Figure 1A:
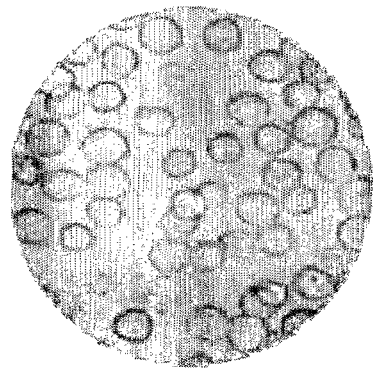
FIG. 1A shows a microscopic image of normal cells.

The present invention provides a novel type of fermented soybean that has excellent characteristics, is inexpensive, and can be used in various applications.

Technical Solution

To achieve this, the inventors of the present invention tried to ferment a composition including a folic acid and soybean extract and produced a novel folyl extract of fermented soybean (folyl EFS).

Advantageous Effects

A folyl extract of fermented soybean (folyl EFS) according to the present invention inhibits mast cells from generating histamine, wherein the phenomenon in which mast cells generate histamine is one of the symptoms occurring in people who have serious cutaneous adverse reactions such as allergy. Also, the folyl EFS is very effective for alleviating anaphylaxis. In addition, the folyl EFS promotes absorption of minerals such as calcium in the small bowel, and promotes femurs (thigh bones) growth of mammals. Furthermore, the folyl EFS promotes biosynthesis of collagen due to its cell activation function and thus, when applied to human skin, a wrinkle-improvement effect can be obtained and thus, various other effects, such as moisturizing and anti-allergic effects, can also be obtained. Also, the folyl EFS protects cells from being damaged by ultra-violet (UV) radiation. Accordingly, the folyl EFS and a composition including the folyl EFS can be used in health supplement foods, cosmetics, skin external applications, pharmaceutical products, and livestock feeds. Also, the folyl EFS according to the present invention can be produced at lower costs and in higher yields than other products having similar effects.

MODE OF THE INVENTION

The present invention is directed to a folyl extract of fermented soybean (folyl EFS) produced by fermenting a culture including a folic acid and soybean extract using a microorganism and an application thereof.

γ-polyglutamate is generated when soybeans are fermented using a microorganism and is a polymer in which an amine group of a glutaminic acid is peptide-linked to γ-carboxyl group. Meanwhile, the folic acid (Vitamin B9 or pteroyl glutamic acid) is a glutamic acid analog in which a glutamic acid binds to a pteroyl ring. The inventors of the present invention identified that y-polyglutamate, which is conventionally produced when soybeans are fermented, can be generated by synthesis enzymes produced by a microorganism of the genus *Bacillus*, and conducted experiments based on the fact that when synthesis enzymes are brought into contact with the folic acid in which the pteroyl ring binds to the glutamic acid, synthesis enzymes are inclined to polymerize the folic acid. As a result, the inventors of the present invention found that when the folic acid is added when soybeans are fermented using a microorganism, the folic acid is incorporated into γ-polyglutamate by enzymes produced by the microorganism and thus, a new type of polymer, that is, folyl polyglutamate including the folic acid and the glutamic acid can be mass-produced. Accordingly, the present invention provides a folyl EFS and a method of mass-producing the folyl EFS. The folyl EFS according to the present invention includes folyl polyglutamate. Also, the folyl EFS according to the present invention may include levan (microbial polyfructan) that is produced when soybeans are fermented.

The folic acid incorporated in the folyl EFS has very different characteristics from a folic acid on its own, and has high solubility with respect to water and thus, can be more efficiently used in industrial applications and more easily absorbed into small bowels of animals.

Also, since the folyl EFS according to the present invention may also include levan (microbial polyfructan) that is produced when soybeans are fermented, growth of *bifidus lactobacillus* can be promoted and thus, cleaning effect of stomach and intestines and an obesity prevention effect can be obtained.

The folyl EFS according to the present invention also has a higher immunostimulating effect and an anti-allergic effect in proportion to the concentration of the folyl EFS, which has been identified through in vitro tests and animal tests. A folic acid itself does not have those immunostimulating and anti-allergy effects. The folyl EFS according to the present invention inhibits secretion of histamine (see FIGS. 1 and 2), and alleviates anaphylaxis (see FIG. 3). Accordingly, the folyl EFS according to the present invention can be used in food products for preventing acute allergy in babies and children and improving constitution of adults. Also, the folyl EFS according to the present invention can be used in a skin external application or cosmetic composition for alleviating atopic dermatitis or allergies.

Figure 6:
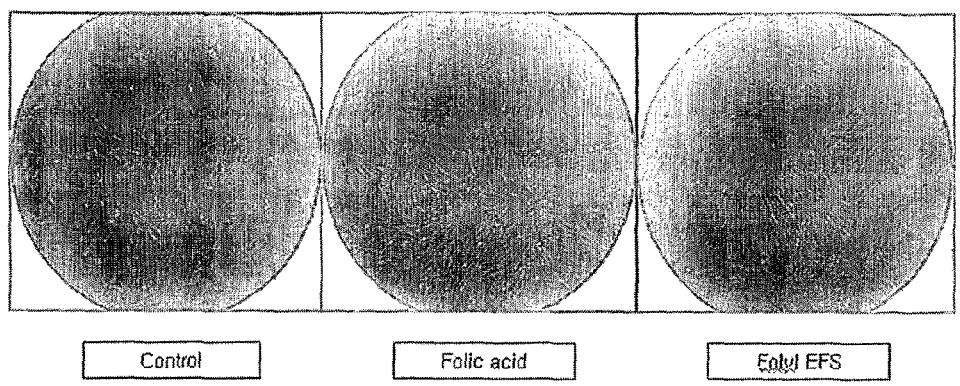
FIG. 6 shows microscopic images of the primary culture of a fibroblast with a folyl EFS or a folic acid, after being incubated in a fibroblast culture medium (FGM, KDR Co.) for 24 hours.

The folyl EFS according to the present invention promotes biosynthesis of collagen (see FIG. 6), and has a wrinkle-improvement effect (see Table 5). Accordingly, the folyl EFS according to the present invention can be used in moisturizing, skin-improving external applications or cosmetic compositions based on metabolism activation, and has a wrinkle-improvement characteristic and effects caused as a result thereof.

Figure 4:
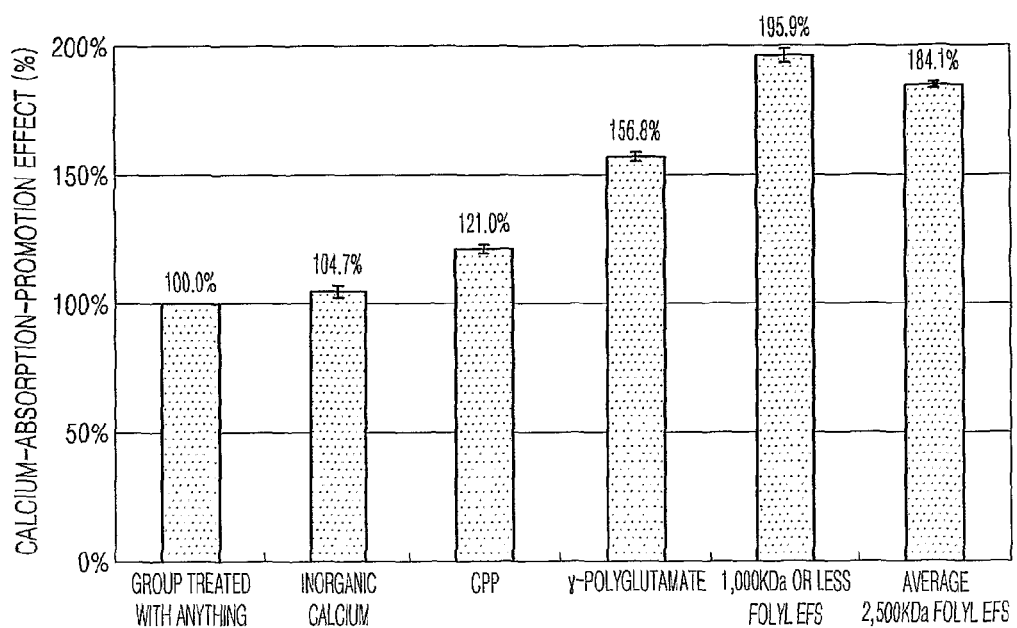
FIG. 4 is a bar chart of test results showing a calcium-absorption-promotion effect of a folyl EFS in small bowels of animals, wherein, in an experiment to obtain the results, the animals are given the folyl EFS added feed, small bowels of the animals were separated and calcium of each group was quantified, and the quantified results were represented in a ratio with respect to a group given nothing added feed.

The folyl EFS according to the present invention promotes absorption of calcium in small bowels of animals (see FIG. 4). Accordingly, the folyl EFS can be used together with a pharmaceutical metal such as calcium, iron, or manganese, and thus various products can be produced including, in addition to functional products, pharmaceutical products, such as nutrition suppliers, anti-anemic agents for pregnant women, or diabetes supplements.

Figure 5:
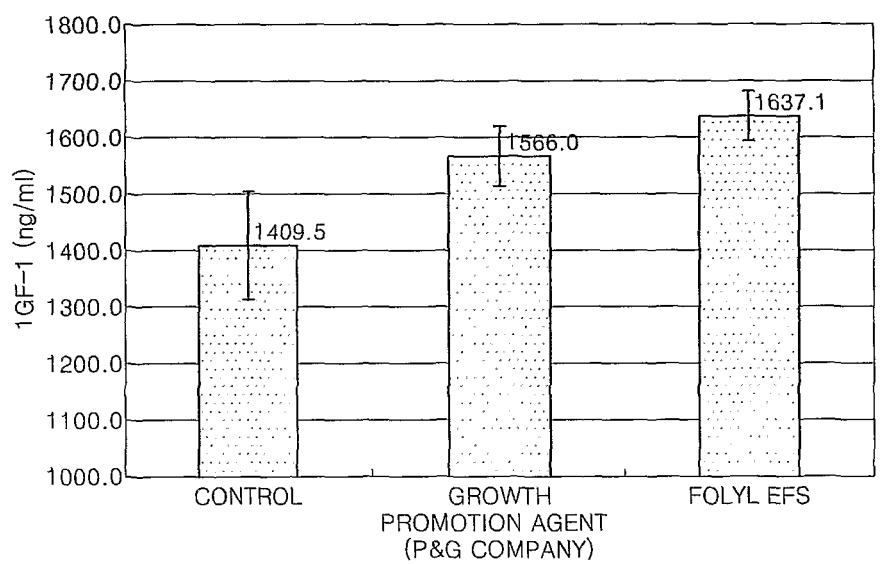
FIG. 5 is a bar chart of test results showing a growth promotion effect of a folyl EFS, wherein, in an experiment to obtain the results, rats were fed the folyl EFS for a predetermined period of time, blood was taken from each group, and IGF-1 in the blood was quantified by ELISA.

Also, the folyl EFS according to the present invention promotes bone growth (see Table 4), and increases growth factors in blood (IGF-10) (see FIG. 5). An example of a currently available growth promoting material is KI-180 which has been co-developed by Highki growth clinic and the Korea Food Research Institute. KI-180 is expensive because it is extracted from herbal medicines and thus is used in expensive pharmaceutical products, not food products. Thus, it is difficult to commercialize KI-180. However, since the folyl EFS according to the present invention can be mass-produced through fermentation with a microorganism, the folyl EFS can be used in a wide range of applications, such as functional foods for children, osteoporosis-prevention-functional foods for postmenopausal women, and nutrition suppliers. Thus, the folyl EFS can be more easily commercialized than conventional growth promoting materials.

Based on the experimental results described above, the present invention provides:

[1] The folyl EFS, including folic acid polyglutamate as a major component, wherein the folyl EFS is produced by fermenting a culture including a folic acid and soybean extract by using a microorganism;

[2] The folyl EFS of [1], wherein the microorganism is selected from a genus *bacillus* microorganism or a genus *corynebacterium* microorganism;

[3] The folyl EFS of [1], wherein the microorganism is *Bacillus subtilis;*

[4] The folyl EFS of any one of [1] to [3], wherein the folyl EFS has an is anti-histamine effect;

[5] The folyl EFS of any one of [1] to [3], wherein the folyl EFS has an anti-allergic effect;

[6] The folyl EFS of any one of [1] to [3], wherein the folyl EFS has a calcium-absorption-promotion effect;

[7] The folyl EFS of any one of [1] to [3], wherein the folyl EFS has a bone-growth-promotion effect;

[8] The folyl EFS of any one of [1] to [3], wherein the folyl EFS has a collagen-biosynthesis-promotion effect;

[9] The folyl EFS of any one of [1] to [3], wherein the folyl EFS has a wrinkle-improvement effect;

[10] The folyl EFS of any one of [1] to [3], wherein the folyl EFS has a cell-growth-promotion effect;

[11] A composition for skin external application or cosmetics, including the folyl EFS of any one of [1] to [3] as an active component;

[12] The composition for skin external application or cosmetics of [11], wherein the composition is used for anti-allergic or improving atopic dermatitis;

[13] The composition for skin external application or cosmetics of [11], wherein the composition is used to activate metabolism of skin cells, prevent formation of wrinkles, or improve the appearance of wrinkles;

[14] The composition for skin external application or cosmetics of [11], wherein the composition is used to inhibit cell damage caused by ultra-violet (UV) radiation;

[15] A health supplement food composition, including the folyl EFS of any one of [1] to [3] as an active component;

[16] The health supplement food composition of [15], wherein the health supplement food composition is used in drinks;

[17] The health supplement food composition of [15], wherein the health supplement food composition has a growth promotion effect;

[18] The health supplement food composition of [15], wherein the health supplement food composition has an osteoporosis prevention effect;

[19] The health supplement food composition of [15], wherein the health supplement food composition has a calcium-absorption-promotion effect;

[20] The health supplement food composition of [15], wherein the health supplement food composition prevents occurrence of allergy or improves constitution;

[21] A feed composition, including the folyl EFS of any one of [1] to [3] as an active component;

[22] A pharmaceutical composition for promoting cell growth, including the folyl EFS of any one of [1] to [3] as an active component;

[23] A pharmaceutical composition for treating or preventing osteoporosis, including the folyl EFS of any one of [1] to [3] as an active component;

[24] A pharmaceutical composition for promoting absorption of calcium, including the folyl EFS of any one of [1] to [3] as an active component; and

[25] A method of manufacturing a folyl extract of fermented soybean (EFS) by fermenting a culture including a folic acid and soybean extract by using a microorganism.

The folyl EFS according to the present invention may be produced using soybean extract. A method of producing soybean extract will now be described in detail. Soybeans are added to distilled water, wherein the ratio of soybeans to distilled water is about 0.1% to about 50%. The mixture is heated at 100° C. for 1 to 2 hours and slowly cooled and then, a solid content is removed therefrom, thereby completely producing the soybean extract. A medium is prepared using 0.1 to 25% of glucose, 0.01 to 10% of $Na_2HPO_4$, and 0.01 to 10% of $NaH_2PO_4$. Then, 0.1 to 90% of the soybean extract and 0.01% to 10% of a folic acid are added to the medium, the resultant medium is sterilized, and then *Bacillus subtilis* separated from foods is inoculated into the medium and a fermentation process is performed at a temperature of 10 to 60° C., and specifically of 35 to 55° C., at pH of 5.5 to 8.5, in facultative fermentation conditions, for 48 to 96 hours. After the fermentation process is complete, non-soluble materials such as cells are removed through continuous centrifugation and the pH of the resultant solution is controlled using 2M HCl to be pH 3 to 5, specifically pH 4. Then, ethanol is added thereto wherein the amount of ethanol is two or more times greater than that of the pH-controlled solution. As a result, a folyl EFS is obtained and lyophilized and preserved in powder. Grouping according to molecular weight may be performed using a conventional method. For example, the grouping may be performed by chromatography or using a cross-flow ultrafiltration unit.

A microorganism that can be used to ferment a folic acid and the soybean extract used in the present invention may be a genus *Bacillus* microorganism or genus *Corynebacterium* microorganism which is capable of producing γ-polyglutamate. Examples of the genus *Bacillus* microorganism include *Bacillus subtilis*, *Bacillus anthracis*, *Bacillus lichenifonnis*, and *Bacillus megaterium*. For example, the genus *Bacillus* microorganism may be *Bacillus subtilis*. The genus *Corynebacterium* microorganism may be *Corynebacterium glutamicum*, but is not limited thereto.

Also, the folyl EFS has an anti-allergic effect and promotes the growth of animal including human and *Bifidobacterium* and *Lactobacillus* growth, and thus contributes to high livestock profit and high meat quality. Accordingly, the folyl EFS can be used as feed additives in the animal feed industry.

A composition according to the present invention may include the folyl EFS, wherein the amount of the folyl EFS may be 0.01 to 60 wt. %, specifically 0.1-50 wt. %, of the composition.

In a cosmetic composition according to the present invention, the folyl EFS may be used together with appropriate amounts of components that are used in a conventional skin cosmetic material. Examples of such components include an oil material, water, a surfactant, a moistening agent, lower alcohol, a thickener, a chelating agent, a colorant, a preservative, and perfumes. The cosmetic composition including the folyl EFS according to the present invention may be used in moisturizing cosmetic products, face cleansing products, or other cosmetic products, but is not limited thereto. Specifically, the cosmetic composition including the folyl EFS according to the present invention can be used in cosmetic products, such as astringent cosmetic water, emollient cosmetic water, nutrient cosmetic water, various creams, essence, packs, or foundations; cleansing products; face cleansing products; soap; treatments; or cosmetic solutions. More specifically, the cosmetic composition including the folyl EFS according to the present invention can be used in skin lotion, skin softener, skin toner, astringent lotion, milk lotion, moisturizing lotion, nutrient lotion, massage cream, nutrient cream, moisturizing cream, hand cream, essence, nutrient essence, packs, soap, shampoo, cleansing foams, cleansing lotion, cleansing cream, body lotion, body cleanser, oil material, press powder, loose powder, or eye shadow.

A pharmaceutical composition according to the present invention may be used in a solid, semi-solid, solution, or oil form, or in a form of a dispersant, a micelle, or a liposome. The pharmaceutical composition may include: an organic or inorganic carrier or an excipient that is suitable for intestinal or non-oral administrations; and the folyl EFS according to the present invention as an active component. The active component can be mixed with a conventionally non-toxic pharmaceutically acceptable carrier that is suitable for, for example, a tablet formulation, a pellet formulation, a capsule formulation, is a suppository formulation, a solution formulation, an oil formulation, a suspension formulation, an ointment formulation, or any type of formulation that is easily used. An available carrier may be glucose, lactose, gum arabic, gelatin, mannitol, starch paste, magnesium salt trisilicate, talc, corn starch, keratin, colloidal silica, potato starch, urea, triglyceride having an intermediate chain length, or any type of carrier that is suitable for manufacturing formulations, which may be solid, semi-solid, or liquid. The pharmaceutical composition may further include a supplement, a stabilizer, a thickener, a colorant, or a perfume. The pharmaceutical composition including the active component may be formed in any formulation that can be easily orally administered, for example, a tablet formulation, troche, a lozenge-shaped tablet formulation, an aqueous or oil suspension formulation, a dispersible powder formulation, a granule formulation, a oil, hard or soft capsule formulation, a syrup formulation or an elixir formulation. These compositions for oral administration may be prepared using any method that is used to manufacture a pharmaceutical composition and known in the art. To obtain excellent pharmaceutical characteristics and make these compositions for oral administration more attractive in terms of flavor, the compositions for oral administration may further include at least one functional agent selected from the group consisting of a sweetener such as sucrose, lactose or saccharin; a favoring agent such as peppermint, pyrola japonica, or cherry; a colorant; and a preserving agent. A tablet including an active component and a non-toxic pharmaceutically acceptable excipient can be produced using a conventional method. The non-toxic pharmaceutically acceptable excipient may be: a non-active excipient such as calcium carbonate, lactose, a calcium phosphoric acid or a sodium phosphoric acid; a granulating agent or decomposing agent, such as corn starch, potato starch or an alginic acid; a binder such as tragerkans rub, a corn potato, gelatin, or Acasia; or a lubricant such as magnesium stearic acid, stearic acid, or talc. The tablet may be not coated, or may be coated using a conventional method to delay the decomposition or absorption of the tablet in the gastrointestine and thus to sustain the pharmaceutical effect for a longer period of time. A delaying material for this purpose may be glyceryl monostearate or glyceryl distearate. Those materials can also be used to form an osmotic treatment tablet formulation to control emission of the active component.

In some cases, an oral formulation may be a hard gelatin capsule in which an active component is mixed with a non-active solid diluent, for example, calcium carbonate, calcium phosphoric acid, or kaolin, or a soft gelatin capsule in which an active component is mixed with water or an oil medium, such as peanut oil, liquid paraffin, or olive oil.

Since subjects to be treated have various symptoms and drugs have particular therapeutic characteristics, determining responses of subjects with respect to treatments and changing administration dosages according to responses should be conducted by experts. Typically, a daily administration dosage may be about 10 μg to about 200 mg/body weight (kg), specifically about 50 μg to about 100 mg/body weight (kg). A daily administration frequency may be four times or less.

A food composition including the folyl EFS according to the present invention may be used to produce various foods. Examples of such foods include meats, sausages, bread, chocolates, candies, snacks, confectionery, pizza, various types of noodles, gums, dairy products including ice cream, various soups, beverages, teas, drinks, alcoholic drinks, and vitamin composites, but the present invention is not limited thereto.

The present invention will be described in further detail with reference to the following examples and experimental examples. These examples and experimental examples are for illustrative purposes only and are not intended to limit the scope of the present invention.

Example 1

Production of Folyl EFS

To produce a folyl extract of fermented soybean (folyl EFS), first, soybean extract was prepared. Specifically, soybeans were added to distilled water, wherein the ratio of soybeans to distilled water was 50% and the mixture was heated at 100° C. for 1 hour and slowly cooled and then, a solid content was removed therefrom, thereby producing soybean extract. A medium was prepared using 2.0% of glucose, 1.0% of $Na_2HPO_4$, and 0.5% of $NaH_2PO_4$. Then, 90% of the soybean extract and 0.5% of the folic acid were added to the medium, the resultant medium was sterilized, and then Bacillus subtilis separated from foods was inoculated into the medium and a fermentation process was performed at a temperature of 45° C. for 72 hours. After the fermentation process was complete, non-soluble materials such as cells were removed through continuous centrifugation and the pH of the resultant solution was controlled using 2M HCl to be pH 4. Then, ethanol was added thereto wherein the amount of ethanol was two or more times greater than that of the pH-controlled solution. As a result, a folyl EFS was obtained and lyophilized and preserved in powder. To produce a polymer having a molecular weight of 1000 KDa, polymers having a molecular weight of 500 KDa or less were removed using Sepharose 4B, and the remaining solution were divided using a cross-flow ultrafiltration unit (produced by Vivascience Co.) into a fraction containing polymers having a molecular weight of 1,000 KDa or more and a fraction containing polymers having a molecular weight of less than 1,000 KDa. The average molecular weight of the fraction of polymers having the molecular weight of 1,000 KDa or more was measured through gel permeation chromatography (GPC) using liquid chromatography (LC) and the measured average molecular weight was 2,500 KDa. These two fractions were dried and used in the same powder amount.

Example 2

Production of Composition Including the Folyl EFS

Various compositions including 0.0 to 10.0 wt. % of the folyl EFS prepared in Example 1 and additives which can be used in foods and medicines were prepared.

(1) Preparation Example 1

Food Composition Including Folyl EFS

Food compositions that include components and amounts thereof as shown in Table 1 were prepared to produce drinkable health supplement foods. In these compositions, the amount of refined water was appropriately controlled according to the amount of natural preservative.

TABLE 1

Food compositions including folyl EFS (wt. %)

| Component | Composition 1 | Composition 2 | Composition 3 | Composition 4 | Composition 5 | Composition 6 |
|---|---|---|---|---|---|---|
| Folyl EFS prepared in Example 1 | — | — | 0.05 | 0.1 | 0.2 | 0.3 |
| Cromoline sodium salt | — | 1 | — | — | — | — |
| Cyclodextrin | 2 | 2 | 2 | 2 | 2 | 2 |
| Trace amounts of additives such as minerals | 3 | 3 | 3 | 3 | 3 | 3 |
| Distilled water | 95 | 94 | 94 | 94 | 94 | 94 |
| Natural preservative | appropriate | appropriate | appropriate | appropriate | appropriate | appropriate |

(2) Preparation Example 2

Cosmetic Composition Including Folyl EFS

Cosmetic compositions that included components and amounts thereof as shown in Table 2 and a control composition including distilled water instead of the folyl EFS were formulated. In Table 2, (A) represents water-soluble materials, and (B) represents oil-soluble materials. The amount of the sterilized distilled water was appropriately controlled according to amounts of preservative, flavor material, and pigment.

TABLE 2

Cosmetic compositions including folyl EFS (wt. %)

| | Component | Composition 1 | Composition 2 |
|---|---|---|---|
| A | Ethanol | 5.0 | 5.0 |
|   | Folyl EFS prepared in Example 1 | — | 1.0 |
|   | Glycerin | 4.0 | 4.0 |
|   | 1,3-butyleneglycol | 4.0 | 4.0 |
|   | Sterilized distilled water | 68.5 | 67.5 |
| B | Ethanol | 5.0 | 5.0 |
|   | Cetyl alcohol | 1.0 | 1.0 |
|   | Bees wax | 0.5 | 0.5 |
|   | Vaseline | 2.0 | 2.0 |
|   | Squalene | 6.0 | 6.0 |
|   | Dimethylpolysiloxane | 2.0 | 2.0 |
|   | POE(10)monooleic acid Ester | 1.0 | 1.0 |
|   | Glycerol monostearinic acid Ester | 1.0 | 1.0 |
|   | Preservative | appropriate | appropriate |
|   | Flavor material | appropriate | appropriate |
|   | Pigment | appropriate | appropriate |

(3) Preparation Example 3

Feed Composition Including Folyl EFS

Feed compositions that included components and amounts thereof as shown in Table 3 were prepared.

TABLE 3

Feed compositions including folyl EFS (wt. %)

| Component | Composition 1 | Composition 2 |
|---|---|---|
| Folyl EFS prepared in Example 1 | — | 1 |
| Calcium carbonate | 70 | 70 |
| zeolite | 30 | 29 |

Example 3

Anti-Allergy Test

Example 3-1

Anti-Histaminic Effect Identified by Observing Mast Cells Through Microscopy

Figure 1B:
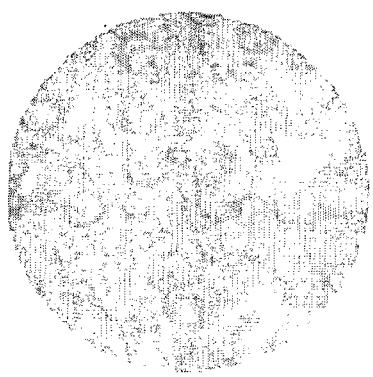
FIG. 1B shows a microscopic image of cells 30 minutes after the cells were treated with a stimulant.
Figure 1C:
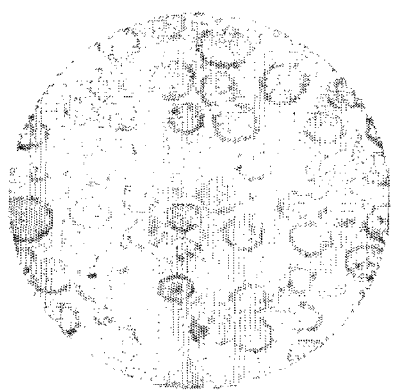
FIG. 1C shows a microscopic image of cells 30 minutes after the cells were treated with a folyl EFS and a stimulus.

To identify the anti-histamine effect of the folyl EFS, a test material was applied to mast cells (ATCC TIB-64, P815) and observed the mast cells through microscopy (see George Chiang et al, The Journal of Urology, December, 164, 2000, p 2119~2125). FIG. 1A shows an image of normal mast cells, FIG. 1B shows an image of mast cells which were treated with 10 ug/ml of C48/80(sigma) as a stimulant and placed left for 30 minutes, and FIG. 1C shows an image of mast cells which were treated with the folyl EFS and the stimulant, and placed left for 30 minutes. Referring to FIGS. 1A to 1C, normal mast cells were round and smooth. Mast cells were rough when an immune reaction occurred. However, when mast cells were treated with C48/80 as a stimulant and placed left for 15 minutes, mast cells were distorted and had protrusions on surfaces thereof, and when 30 minutes had passed, mast cells completely lost their original shapes and burst, thereby secreting histamine. The distortion of surfaces of mast cells is a phenomenon in which various signal delivery materials are secreted from cell membranes of mast cells stimulated by C48/80 and stability of cell membranes is degraded, and thus surfaces of the cell membranes are unstable. Accordingly, the anti-histamine effect can be identified based on how well the original surface shapes of mast cells are maintained after the C48/80 treatment. However, when treated with the folyl EFS and placed left for 15 minutes, mast cells retained their original shapes, and even when 30 minutes had passed, only a small number of the cells secreted histamine and cell membranes thereof burst.

Example 3-2

Anti-Histaminic Effect Identified by Quantifying Histamine of Mast Cells

Figure 2:
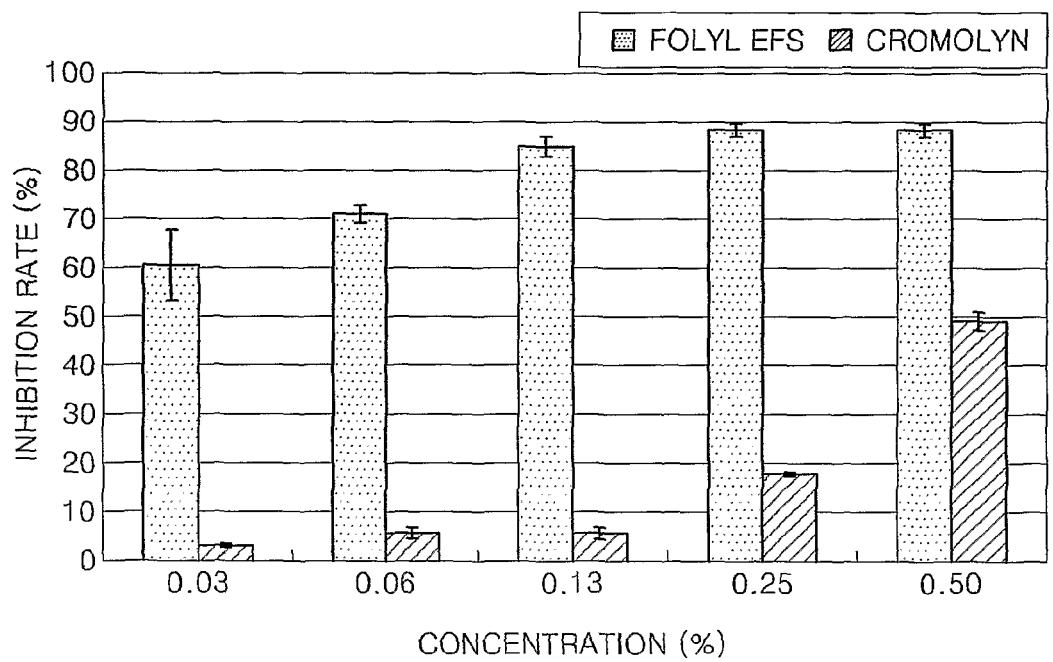
FIG. 2 is a bar chart of test results showing a histamine-secretion-inhibition effect of a folyl EFS by quantifying histamine and cromolyn that is known as a therapeutic agent for asthma.

This experiment was performed to identify how much the folyl EFS reduces the amount of histamine secreted when mast cells are treated with a stimulant. The amount of histamine secreted was quantified using ELISA. 1% sodium cromolyn, which is known as an asthma treatment drug, was used as a control group, and C48/80 was used as a stimulator to induce activation of mast cells (ATCC TIB-64, P815). FIG. 2 is a bar chart showing the results of the experiment.

Referring to FIG. 2, when about 0.5% of the sodium cromolyn as an asthma to treatment drug was used, a histamine secretion inhibition rate was 50% and thus, an ED50 value was 0.5%, and when the folyl EFS was used, an ED50 value was about 0.063%, 8 times lower than that when the sodium cromolyn was used. As described above, it can be seen that the folyl EFS has an excellent anti-histamine (anti-allergic) effect.

Example 3-3

Anti-Allergic (Anti-Anaphylaxis) Tests

Figure 3:
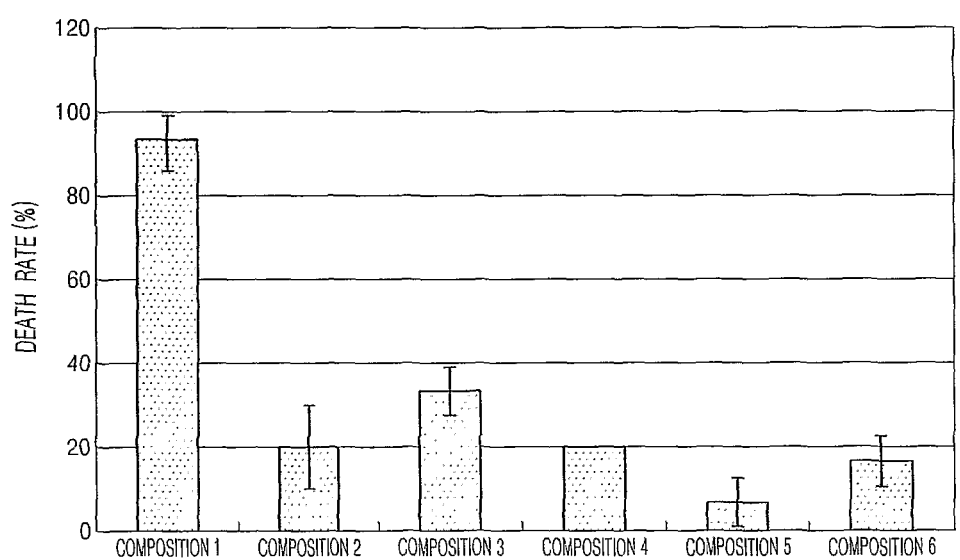
FIG. 3 is a bar chart showing test results of the folyl EFS with respect to anaphylaxis, represented in a death rate of each group when a stimulus is intraperperitoneally injected.

To confirm the anti-histamine effect of the folyl EFS, which has been identified in Example 3-1 in animals, mice were fed Compositions 1-6 used in Preparation Example 1 for 7 days and then, C48/80 was intraperperitoneally injected thereto to induce anti-anaphylaxis. FIG. 3 is a bar chart showing the results of the experiment.

C48/80 is a material that stimulates immune organs and induces acute anaphylaxis within 30 minutes when intraperperitoneally injected. In the current experiment, the number of test animals which died within a predetermined time period (24 hours) after the intraperperitoneal injection of the C48/80 was counted. In the current experiment, 10 mice (BALB/C, male) were used per group, and each group was tested for three times and the average value of the three experimental results was represented as a death ratio (%).

Referring to FIG. 3, the death rate of a group fed with Composition 1 to which nothing was added was 93.3% and 9 out of 10 mice died within 24 hours after C48/80 was injected. The death rate of a group fed with Composition 2 to which the sodium cromolyn was added, that is, the death rate of the control group, was 20%. Experimental groups were respectively fed with Compositions 3 to 6 to which the folyl EFS having various concentrations of 0.05 to 0.3% were added. The death rate of the experimental group of Composition 3 to which 0.05% of the folyl EFS was added was 33.3%, the death rate of Composition 4 was 20%, the death rate of Composition 5 was 6.7%, and the death rate of Composition 6 was 16.7%. In consideration of these results, it can be seen that 1% sodium cromolyn as an asthma treatment drug inhibits development of anaphylaxis up to 80% and the folyl EFS inhibits development of anaphylaxis up to 94% at the concentration of 0.2%. However, the mice which survived within 24 hours after the stimulus C48/80 was injected developed abnormally swollen anuses. Such incident was found in about 80% of the mice to which Composition 2 including sodium cromolyn, and about 10%, 0%, 0%, and 0% when Compositions 3 through 6 including various concentrations of folyl EFS were respectively used. Accordingly, it can be seen that sodium cromolyn inhibited development of anaphylaxis and prevented death of mice but did not inhibit sequela of anaphylaxis, and the folyl EFS inhibited the sequela of anaphylaxis as well as death of mice.

Example 4

Calcium Absorption Promotion Effect

The current experiment was performed using mice (BALB/C, male) and each feed was orally administered to mice two times per day. The oral administration period was 3 days and after the oral administration period, small bowels of the mice were isolated. The obtained small bowels were washed with saline 3 or more times, and tissues of the small bowels isolated from each group were ground with a teflon homogenizer. The obtained product was centrifuged and the supernatant was isolated. Then, the amount of calcium absorbed into the small bowels was measured using a calcium quantification kit (Wako Co.). FIG. 4 is a bar chart showing the results of the experiment.

Referring to FIG. 4, a group given with the folyl EFS added feed had about 84 to 96% increase of a calcium absorption rate compared to a control group given nothing added feed. A calcium absorption rate of a group given calcium salt added feed was about 4.7%, a group given casein phosphopeptide (CPP) added feed was about 21%, and a group given γ-polyglutamate added feed was about 56.8%. For the folyl EFS, when the molecular weight was 500 to 1,000 KDa, the calcium absorption rate was higher than when the molecular weight was higher than 1,000 KDa. Such a result may be because when the molecular weight of the folyl EFS is too high, a calcium ion, that is a bi-valent ion, reacts with the folyl EFS having a negative charge and thus, non-soluble precipitate may be produced. Accordingly, it is desirable that a calcium-folyl EFS composite is produced to be soluble when the molecular weight of the folyl EFS is high.

Example 5

Growth Promotion Effect

Since, as described in Example 3, the folyl EFS promoted absorption of calcium into bowels, the current experiment was performed to identify whether the calcium absorbed into bowels affects animal bone growth and growth factors in blood (IGF-1). Mammals were given folyl EFS added feed for two weeks, and the length and weight of femurs (thigh bones) of the mammals were measured and blood was taken to measure IGF-1 that is the growth factor. The results were compared with those of a control group given saline added feed. The tested mammals were four-week old rats (SD rat, male). A comparative group was given "Kikerup gold" product containing as a major to component herb extracts of Acantopanax, a red flower seed, Rehmanniae radix preparata, Poria cocos, Dioscoreae rhizoma, Corni fructus, antler etc., which is produced by a P&B company, and tested under the same condition as when the folyl EFS was used.

The results are shown in Table 4 and FIG. 5.

When the standard error was 5% or less, the femurs (thigh bones) of the control group fed with saline had an average length of 29.22 mm, the femurs (thigh bones) of the comparative group fed with the growth promotion product of the P&B company had an average length of 29.63 mm, and the femurs (thigh bones) of the experimental group fed with the folyl EFS had an average length of 30.04 mm. Compared to the control group, the comparative group had a growth promotion effect of about 1.4% and the experimental group had a growth promotion effect of about 3.1% (Table 4). IGF-1, which is known as a growth promotion factor in blood, was quantified by ELISA. As a result, the control group had 1409.5 μg/ml of IGF-1, the comparative group had 1566 μg/ml of IGF-1, and the experimental group had 1637.1 μg/ml of IGF-1. That is, IGF-1 of the comparative group was 11.1% higher than IGF-1 of the control group, and IGF-1 of the experimental group was 16.2% higher than IGF-1 of the control group (FIG. 5). The weights of the femurs (thigh bones) of the comparative group and experimental group were about 1.3% and about 2.3% higher than that of the control group, respectively. In consideration of those results, it can be seen that the folyl EFS has a growth promotion effect in animals. In addition, when the growth promotion product of the P&B company is compared with the folyl EFS in terms of manufacturing cost, the manufacturing costs of the folyl EFS are about 1/20 of the growth promotion product (Kikerup gold) of the P&B considering that the growth promotion product contains vitamins and nutrients. Accordingly, it is assumed that the folyl EFS has excellent characteristics in terms of various aspects including the manufacturing cost.

TABLE 4

| | Bone growth promotion effect of folic acid | | | | |
|---|---|---|---|---|---|
| Test | Length (mm) | Upper Width (mm) | Middle Width (mm) | Bottom Width (mm) | Weight (mg) |
| Control | 29.22 ± 0.31 | 6.20 ± 0.07 | 2.43 ± 0.03* | 3.64 ± 0.03* | 307.2 ± 9.1 |
| Kikerup gold (P&B) | 29.63 ± 0.15 | 6.24 ± 0.05 | 2.31 ± 0.03 | 3.50 ± 0.05 | 311.2 ± 9.6 |
| Folyl EFS | 30.14 ± 0.16* | 6.22 ± 0.12 | 2.31 ± 0.03 | 3.55 ± 0.05 | 314.3 ± 7.6 |

*P < 0.05, Ducan's multiple test

Example 6

Wrinkle-Improvement Effect and Wound-Healing Effect

Example 6-1

Test Regarding Cell Activation and Collagen Biosynthesis Promotion

The inventors of the present invention found that the folyl EFS has a high cell activation effect. The meaning of the term 'cell activation effect' includes activation of to cell growth, activation of production of metabolites, activation of mitochondria in cells for detoxification, etc. The cell activation effect may induce a skin-wound healing effect and a wrinkle-improvement effect.

Figure 7:
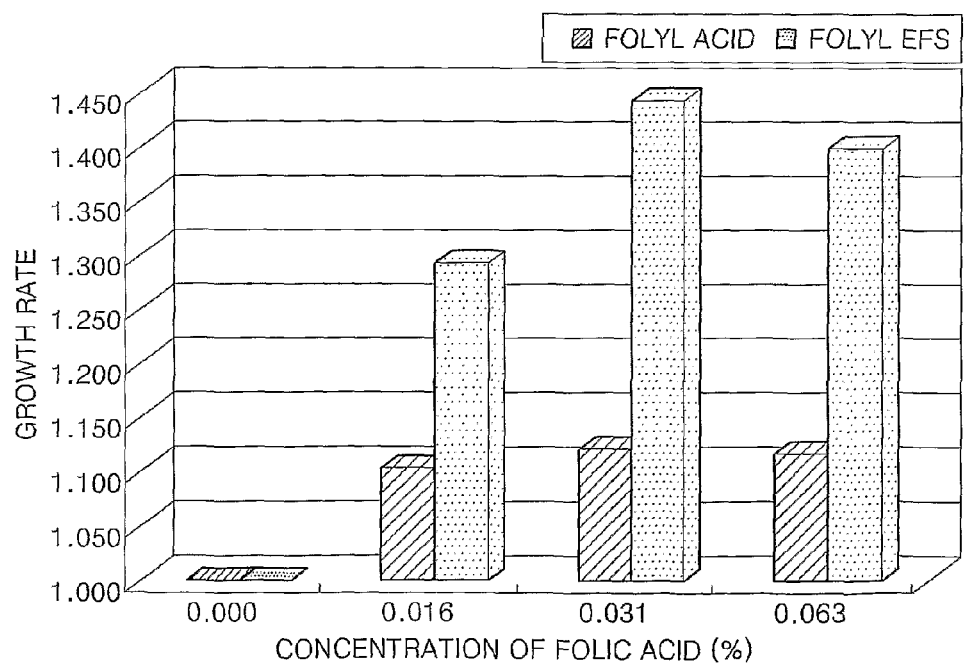
FIG. 7 is a bar chart showing quantification results of viable cells through neutral red (NR) assay after a primary culture of a fibroblast with a folyl EFSor a folic acid, after being incubated in a fibroblast growth medium (FGM, KDR Co.) for 24 hours.

It was identified through the current experiment that the folyl EFS promotes cell growth and collagen biosynthesis. A cell line used in the current experiment was a primary culture of a fibroblast (human dermal fibroblast neonatal; (HDF-N; Gibco, Cooper, M. L. et al, Biomaterials 12:243, 1991), and a culture media used was a fibroblast neonatal growth medium (FGM, KDR Co.). Since the folyl EFS included polyglutamate as a major component in which about 10% of folic acid was incorporated, the folyl EFS was compared with a normal folic acid. $1 \times 10^5$ cells/well of the human dermal fibroblast neonatal and a folic acid or the folyl EFS were incubated for 24 hours, the incubation products were photographed (see FIG. 6), and viable cells were quantified through neutral red (NR) assay (Sigma; Shao-Zeng Z. et al., Cell Biology and Toxicology, 6:2, 1990) (see FIG. 7).

When the folyl EFS was used, the cell growth rate was high, and specifically, when the same concentration of folic acid was used, a higher cell growth rate could be obtained than when only a folic acid was used. In addition, when only a folic acid was used and the concentration of the folic acid was gradually increased, the cell growth rate was not increased accordingly. However, when the folyl EFS was used and the concentration of the folyl EFS was gradually increased, the cell growth rate was distinctively changed accordingly. Such results may stem from a difference in water solubility of the folic acid and the folyl EFS. Specifically, the folyl EFS has high water solubility and thus more cells are affected. Such cell growth promotion leads to a wrinkle-improvement effect when applied in cosmetic products and a wound-healing promotion effect when applied in pharmaceutical products The folyl EFS and the human dermal fibroblast neonatal were incubated for 3 days, and the supernatant was isolated and collagen was quantified using a human collagen type-1 ELISA kit (Cosmo Bio Co.). A sample used in the current experiment was a 1% solution containing Composition 2 used in Preparation Example 2, and 4% of 1,3-butyleneglycol was added to the sample and preserved. Also, to compare with the effect of the folyl EFS, a folic acid solution in which the concentration of the folic acid was the same as that in the folyl EFS was prepared. In addition, 10 ng/ml of transforming growth factor-beta (TGF-β; Sigma), which is known as a promotion factor for collagen biosynthesis, was compared with the folyl EFS.

Figure 8:
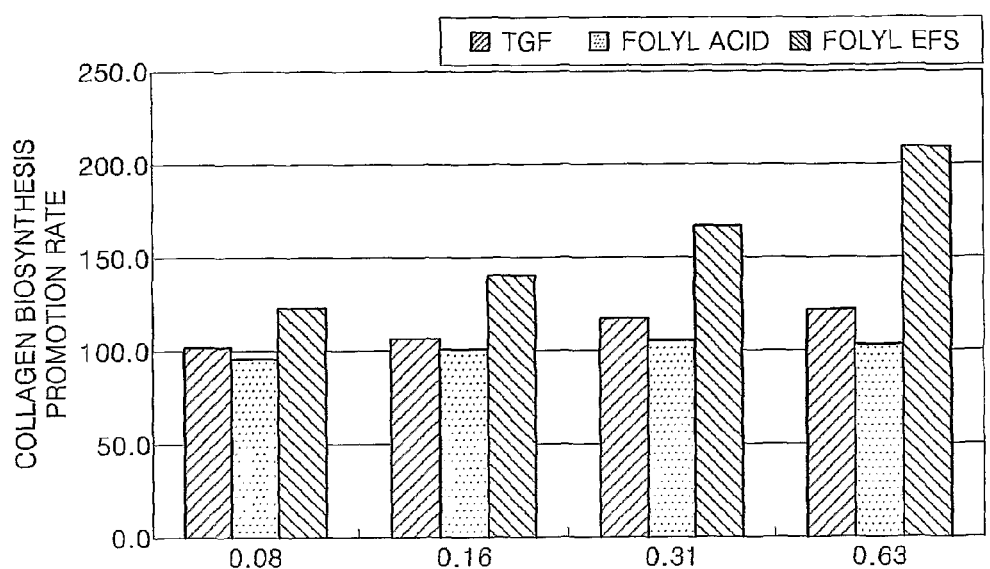
FIG. 8 is a bar chart of results showing a collagen biosynthesis promotion effect of a folyl EFS, wherein, in an experiment to obtain the results, collagen biosynthesis was promoted using a primary culture of a fibroblast and the collagen was quantified by ELISA, and the collagen biosynthesis promotion effect of the folyl EFS was compared with the collagen biosynthesis promotion effect of TGF-β that is known as a collagen biosynthesis promotion material.
Figure 9:
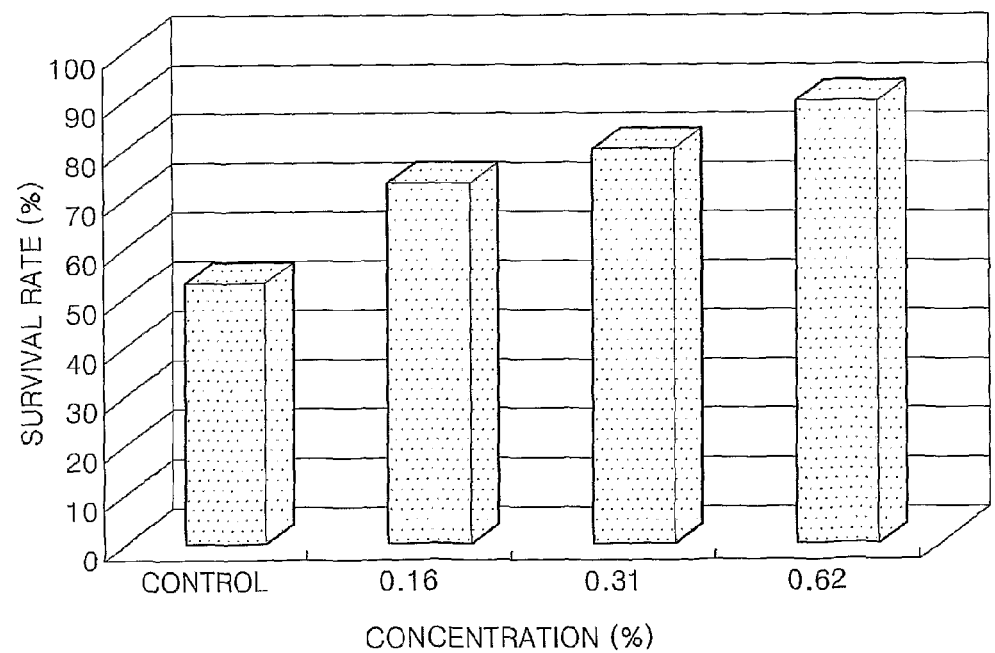
FIG. 9 is a bar chart showing quantification results of viable cells through NR assay, wherein, in an experiment to obtain the results, a primary culture of human keratinocyte was incubated with a folyl EFS in which the content of folic acid was about 10 wt. % in a human keratinocyte growth medium (KGM, KDR Co.) for about 72 hours, ultra-violet (UV) rays having a wavelength of 306 nm were irradiated to grown cells, and then incubated for about 24 hours.

The collagen biosynthesis promotion effect of the folyl EFS is shown in the bar chart of FIG. 8. A folyl EFS produced as a cosmetic source material was a 1% liquid product. In FIG. 8, the concentration (%) of the x-axis denotes a ratio of the volume of the folyl EFS to the volume of the entire culture solution (v/v, %). The results are represented as the ratio of the value of collagen of each group with respect to the average value of collagen in a group not treated with anything when the average value of collagen in the group not treated with anything was set at 100%. As a result, for TGF-β, the maximum promotion rate was 22% at 0.63% (v/v, %), and for the folyl EFS, the maximum promotion rate was 109% at 0.63% (v/v, %). That is, the promotion rate of the folyl EFS was four times higher than that of TGF-β applied to the comparative group, which shows that a wrinkle-improvement effect can be obtained through excess production of collagen in human skin. Meanwhile, when only a folic acid was used, a collagen biosynthesis promotion effect did not occur within an error range. Accordingly, it can be seen that the folyl EFS can be very effectively used as a cosmetic material, specifically, a material for improving the appearance of wrinkles by collagen biosynthesis.

Example 6-2

Test Regarding Wrinkle-Improvement Effect of Cosmetic Composition

To identify a wrinkle-improvement effect of the folyl EFS, Composition 1 (control group) prepared in Example 2 and Composition 2 (experimental group) prepared in Preparation Example 2 were applied to wrinkles surrounding the eyes of 29 women who were 30 year olds two times per day for one month. After one month, the degree of wrinkle appearance improvement was evaluated by referring to questionnaires answered by the subjects and analysis results regarding nutrients of wrinkles. For the questionnaires answered by the subjects, four selective answers were provided to each question, 'no improvement', 'small improvement', 'significant improvement', and 'very significant improvement,' when compared before and after the application.

Wrinkles were evaluated through image analysis. Before the test was performed, replicas below the eyes were collected using Visioscan SV600 (CK Co.), and when the test was finished, replicas were collected from the same position to measure wrinkle density through image analysis. The results are represented as a wrinkle decrease rate The results are shown in Table 5, and it can be seen that when Composition 2 including the folyl EFS was compared with Composition 1, wrinkles were alleviated and the appearance thereof was improved. In addition, when Composition 2 including the folyl EFS was applied, the wrinkle density was reduced to about 45%, compared to that before the application.

Such results show that when the composition according to the present invention is used as a skin external application, the appearance of wrinkles formed in the skin can be effectively improved. Accordingly, it can be seen that the folyl EFS can be effectively used as a cosmetic material.

TABLE 5

Improvement degree and density of skin wrinkles caused by cosmetic compositions

| | No improvement (people) | Small improvement (people) | Significant improvement (people) | Very significant improvement (people) | Wrinkle density (%) |
|---|---|---|---|---|---|
| Composition 1 | 25 | 3 | 1 | 0 | 95 |
| Composition 2 | 0 | 4 | 10 | 15 | 45 |

Example 7

Effect of Inhibiting Cell Damage Caused by Ultra-Violet (UV) Radiation

The inventors of the present invention identified in the current experiment that the folyl EFS inhibits cell damage caused by UV radiation.

$1 \times 10^5$ cells/well of a primary culture of human keratinocyte was incubated in a human keratinocyte growth medium (KGM, KDR Co.) together with a folyl EFS in which the amount of a folic acid was about 10 wt % for about 72 hours, and then UV rays having a wavelength of 306 nm were irradiated to the grown-cells for a predetermined time period. The concentration of folic acid in a final product can be controlled by adjusting the concentration of the folic acid incorporated in the folyl EFS during fermentation. After UV rays were irradiated, the resultant culture was incubated for about 24 hours and viable cells were quantified through an NR assay. The irradiation time period was defined as a time period in which about 50% of the cells died in a preliminary experiment. The results are interpreted as follows:

Survival rate(%)=(growth rate of each group after UV rays were irradiated)/(growth rate of the group having the same concentration which was not exposed to UV radiation).

In media in which folyl EFSs having various concentrations were grown, UV radiation-induced cell damage was inhibited in proportion to the concentration of grown cells. Unlike the results of the cell growth promotion test in Example 6, the highest survival rate was obtained when the concentration of the folic acid was 0.62%. Such a result may be because although the growth rate of cells grown in a medium including about 0.62% of the folyl EFS was lower than that of the growth rate of cells grown in a medium including about 0.31% of the folyl EFS, when about 0.62% of the folyl EFS is used, the UV induced cell damage inhibition rate was higher than when about 0.31% of the folyl EFS was used. Accordingly, it can be seen that when the folyl EFS is added to cosmetic products, ultra-violet (UV) radiation is effectively blocked. Specifically, use of about 0.1-6% of the folyl EFS contributes to an increase in the UV blocking effect in regular formulations, such as lotion and cream, in addition to sun-blocking products.

The invention claimed is:

1. A method of using a composition comprising a folyl extract of fermented soybeans (EFS) for external skin application, comprising the step of administering the composition onto skin of a subject, wherein the composition promotes cell growth, promotes biosynthesis of collagen, or improves the appearance of wrinkles, and wherein the folyl EFS comprises folyl polyglutamate polymer, where folic acid is incorporated into the polyglutamate, as a major component, and the folyl EFS is produced by fermenting a culture comprising 0.1 to 90% of soybean extract and 0.01 to 10% of additionally added folic acid using a microorganism capable of producing the folyl polyglutamate polymer and removing non-soluble materials to obtain the EFS.

2. The method of claim 1 wherein the composition comprises approximately 0.1 to 6% folyl EFS by weight.

3. The method of claim 1 wherein the composition further comprises water, an oil, an alcohol and a surfactant.

4. A method of using a composition comprising a folyl extract of fermented soybeans for external skin application comprising the step of administering the composition onto skin of a subject, wherein the composition inhibits cell damage caused by ultra-violet (UV) radiation, and wherein the folyl EFS comprises folyl polyglutamate polymer, where folic acid is incorporated into the polyglutamate, as a major component, and the folyl EFS is produced by fermenting a culture comprising 0.1 to 90% of and soybean extract and 0.01 to 10% of additionally added folic acid using a microorganism capable of producing the folyl polyglutamate polymer and removing non-soluble materials to obtain the EFS.

5. The method of claim 4 wherein the composition comprises approximately 0.1 to 6% folyl EFS by weight.

6. The method of claim 4 wherein the composition further comprises water, an oil, an alcohol and a surfactant.

* * * * *